United States Patent [19]

Nair et al.

[11] 4,120,953

[45] Oct. 17, 1978

[54] NOVEL 2,2′, 2″-[s-PHENENYLTRIS(SULFONYLIMINO)-TRIS]-[2-DEOXY-α-D-GLUCOPYRANOSE], DODECAKIS (H-SULFATE) COMPOUNDS AND THEIR SALTS

[75] Inventors: Vijay Gopalan Nair, Nanuet; Seymour Bernstein, New City, both of N.Y.

[73] Assignee: American Cyanamid Company, Stamford, Conn.

[21] Appl. No.: 784,491

[22] Filed: Apr. 4, 1977

[51] Int. Cl.$^2$ .............................................. A61K 31/70
[52] U.S. Cl. ........................................ 424/180; 536/4; 536/18; 536/53; 536/54; 536/55; 536/115; 536/118
[58] Field of Search ...................... 424/180; 536/4, 18, 536/53, 54, 55, 115

[56] References Cited

U.S. PATENT DOCUMENTS 2,926,176   2/1960   Linn ........................................ 536/18

*Primary Examiner*—Johnnie R. Brown
*Assistant Examiner*—Blondel Hazel
*Attorney, Agent, or Firm*—Claude J. Caroli

[57] ABSTRACT

Novel 2,2′, 2″-[s-phenenyltris(sulfonylimino)]tris-[2-deoxy-α-D-glucopyranose], dodecakis (H-sulfate) compounds and their salts which are useful as inhibitors of the complement system of warm-blooded animals, and the compound 2,2′,2″-[s-phenenyltris(sulfonylimino)]-tris[2-deoxy-D-glucopyranose] which is a new intermediate for the preparation of the active dodecakis (H-sulfate) compounds.

14 Claims, No Drawings

NOVEL 2,2',2"-[s-PHENENYLTRIS(SULFONYLIMINO)TRIS]-[2-DEOXY-α-D-GLUCOPYRANOSE], DODECAKIS (H-SULFATE) COMPOUNDS AND THEIR SALTS

DESCRIPTION OF THE INVENTION

This invention is concerned with all pharmaceutically acceptable 2,2',2"-[s-phenenyltris(sulfonylimino)]-tris[2-deoxy-α-D-glucopyranose], dodecakis (H-sulfate) compounds and their salts, having complement inhibiting activity, which are novel compounds of the formula (I):

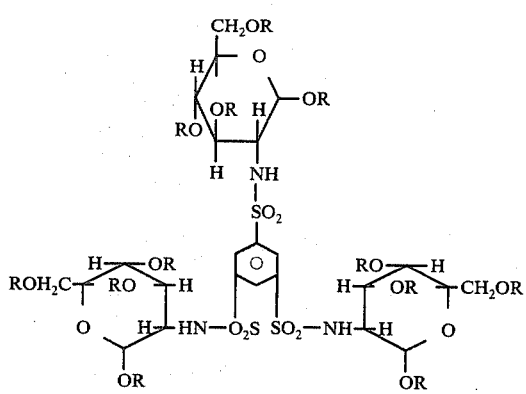

wherein R is a moiety selected from the group consisting of —SO$_3$H.N(CH$_3$)$_3$ and —SO$_3$X, wherein X is selected from the group consisting of alkali metal; and the pharmaceutically acceptable salts thereof.

A preferred embodiment consists of those compounds wherein R is a moiety selected from the group consisting of —SO$_3$X, wherein X is selected from the group consisting of alkali metal.

The aforementioned complement inhibiting dodecakis (H-sulfate) compounds are made from the following novel intermediate:

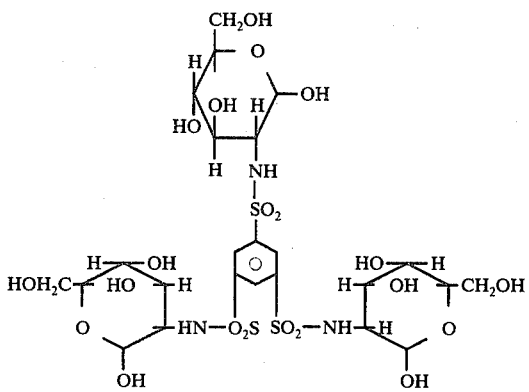

The compounds of the instant invention may be prepared by the following method which is illustrated in Flow Chart A.

The novel intermediate benzene 1,3,5-trisulfonyl tris-glucosamine compound is prepared by reacting tetra-O-acetyl glucosamine (II) with 1,3,5-benzenetrisulfonyl chloride in a weakly basic polar medium such as acetonitrile-pyridine for 24 hours. The solvent is concentrated and the tetraacetyl trisulfonyl derivative (III) is precipitated from ice water and extracted into methylene dichloride. The solvent is evaporated and the material is dissolved in cold methanol saturated with ammonia. Standing in the cold for 24 hours, followed by the addition of nitrogen gas to remove ammonia, produces a thick oil (IV) on evaporation. The oil is purified from water with activated charcoal, filtration and drying to give the intermediate glucopyranose.

Reaction of the above intermediate compound with trimethylamine sulfur trioxide in dimethylformamide at 65°–70° C. for 18 hours followed by precipitation from ethanol produces the novel 2,2',2"-[s-phenenyltris(sulfonylimino)]tris[2-deoxy-α-D-glucopyranose], dodecakis (H-sulfate) dodecasalt with trimethylamine (V), which is an active complement inhibitor.

Treatment of the trimethylammonium salt with sodium acetate in aqueous medium for 15 minutes followed by precipitation from ethanol produces the novel 2,2',2"-[s-phenenyltris(sulfonylimino)]tris[2-deoxy-α-D-glucopyranose], dodecakis (H-sulfate) dodecasodium salt which is also an active complement inhibitor.

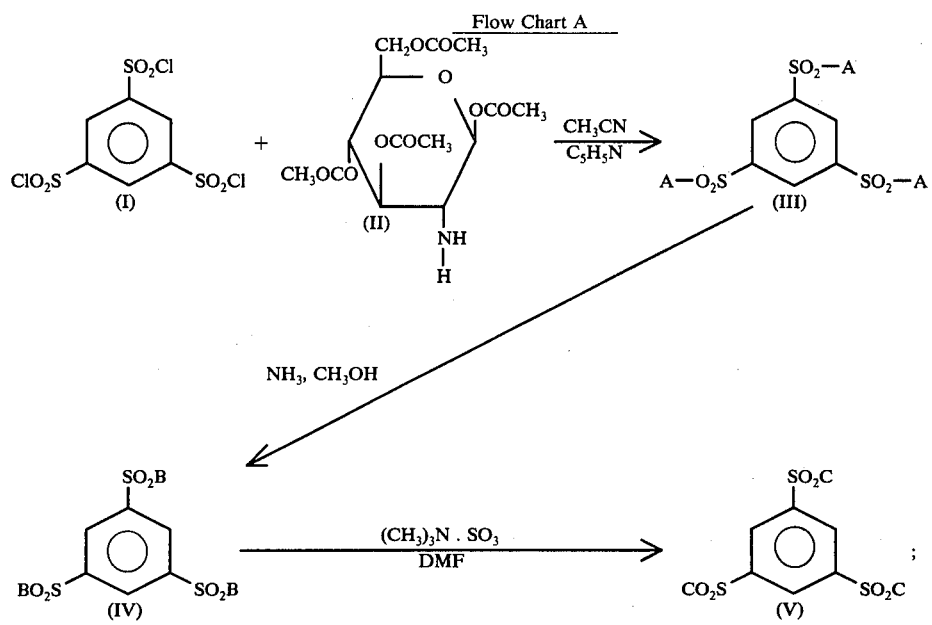

Flow Chart A

In addition, the compound wherein R is the trimethyl ammonium salt may be converted to the sodium salt by hydrolysis.

The term "complement" refers to a complex group of proteins in body fluids that, working together with antibodies or other factors, play an important role as mediators of immune allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, Bull. World Health Org., 39, 935–938 (1968); Ann. Rev. Medicine 19, 1–24 (1968); The John Hopkins Med. J., 128, 57–74 (1971); Harvey Lectures, 66, 75–104 (1972); The New England Journal of Medicine, 287, 452–454; 489–495; 545–549; 592–596; 642–646 (1972); Scientific American, 229, (No. 5), 54–66 (1973); Federation Proceedings, 32, 134–137 (1973); Medical World News Oct. 11, 1974, pp. 53–58; 64–66; J. Allergy Clin. Immunol., 53, 298–302 (1974); Cold Spring Harbor Conf. Cell Proliferation 2/Proteases Biol. Control/229–241 (1975); Annals of Internal Medicine, 84, 580–593 (1976); "Complement: Mechanisms and Functions", Prentice-Hall, Englewood Cliffs, N. J. (1976).

The complement system can be considered to consist of three sub-systems: (1) a recognition unit (C1q) which enables it to combine with antibody molecules that have detected a foreign invader; (2) an activation unit (C1r, C1s, C2, C4, C3) which prepares a site on the neighboring membrane; and (3) and attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389 (1969).

A variety of substances have been disclosed as inhibiting the complement system, i.e., as complement inhibitors. For example, the compounds 3,3'-ureylenebis-[6-(2-amino-8-hydroxy-6-sulfo-1-naphthylazo)]benzenesulfonic acid, tetrasodium salt (chlorazol fast pink), heparin and a sulphated dextran have been reported to have an anticomplementary effect, British Journal of Experimental Pathology, 33, 327–339 (1952). The compound 8-(3-benzamido-4-methylbenzamido)naphthalene-1,3,5-trisulfonic acid (Suramin) is described as a competitive inhibitor of the complement system, Clin. Exp. Immunol., 10, 127–138 (1972). German Patent No. 2,254,893 or South African Patent No. 727,923 discloses certain 1-(diphenylmethyl)-4-(3-phenylallyl)piperazines useful as complement inhibitors. Other chemical compounds having complement inhibiting activity are disclosed in, for example, Journal of Medicinal Chemistry, 12, 415–419; 902–905; 1049–1052; 1053–1056 (1969); Canadian Journal of Biochemistry, 47, 547–552 (1969); The Journal of Immunology, 93, 629–640 (1964); The Journal of Immunology, 104, 279–288 (1970); The Journal of Immunology, 106, 241–245 (1971); and The Journal of Immunology, 111, 1061–1066 (1973).

It has been reported that the known complement inhibitors epsilon-aminocaproic acid, Suramin and tranexamic acid all have been used with success in the treatment of hereditary editary angioneurotic edema, a disease state resulting from an inherited deficiency or lack of function of the serum inhibitor of the activated first component of complement (C1 inhibitor), The New England Journal of Medicine, 286, 808–812 (1972).

EXAMPLE 1

2,2',2''-[s-Phenenyltris(sulfonylimino)]tris[2-deoxy-α-D-glucopyranose], dodecakis (H-sulfate) dodecasalt with trimethylamine A 10.47 g portion of tetra-o-acetyl glucosamine and 3.73 g of 1,3,5-benzenetrisulfonyl chloride in 150 ml of acetonitrile and 10 ml of pyridine is stirred at room temperature for 24 hours. The bulk of the solvent is removed in vacuo and the concentrated solution is poured into 500 ml of ice water with separation of a fine precipitate. The precipitate is extracted into 600 ml of methylene dichloride. The combined extract is washed with water and dried. The solvent is evaporated in vacuo to afford 8.0 g of a pale brown gum.

A 4.0 g portion of the preceding product is dissolved in 50 ml of ice-cold methanol saturated with ammonia. The resulting yellow solution is allowed to stand in an icebox for 24 hours. Nitrogen is bubbled through the solution to remove the ammonia. The solution is evaporated to dryness and the resulting oil is dissolved in distilled water, treated with activated charcoal and filtered through diatomaceous earth. The filtrate is evaporated to dryness in vacuo then is dried in vacuo at 80° C. for 20 hours to give 2.5 g of 2,2',2''-[s-phenenyltris(sulfonylimino)]tris[2-deoxy-D-glucopyranose] as a brown gum.

A 2.0 g portion of the above product is dissolved in 25 ml of dimethylformamide, then 6.0 g of trimethylamine sulfate is added and the mixture is stirred in an oil bath at a bath temperature of 65°–70° C. for 18 hours. The resulting pale brown solution is cooled to room temperature. Upon the addition of absolute ethanol, a thick gum is separated. Subsequent trituration with ethanol provides a fine powder which is collected and washed with ethanol and anhydrous ether to yield 6.2 g of the product of the Example as a pale brown powder

EXAMPLE 2

2,2',2''-[s-Phenenyltris(sulfonylimino)]tris[2-deoxy-α-D-glucopyranose], dodecakis (H-sulfate) dodecasodium salt A 5.0 g portion of the product of Example 1 is dissolved in 20 ml of distilled water, then 20 ml of a 30% aqueous solution of sodium acetate is added and the mixture is allowed to stand for 15 minutes. Addition of 150 ml of absolute ethanol separates a thick gum which is triturated twice with absolute ethanol to provide 3.5 g of a pale brown granular solid as the product of the Example.

EXAMPLE 3

| Preparation of Compressed Tablet | |
|---|---|
| Ingredient | mg/Tablet |
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 4

| Preparation of Compressed Tablet - Sustained Action | |
|---|---|
| Ingredient | mg/Tablet |
| Active Compound as Aluminum Lake*, Micronized | 0.5–500(as acid equivalent) |
| Dibasic Calcium Phosphate N.F. | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 5

| Preparation of Hard Shell Capsule | |
|---|---|
| Ingredient | mg/Capsule |
| Active Compound | 0.5–500 |
| Lactose, Spray Dried | qs |
| Magnesium Stearate | 1–10 |

EXAMPLE 6

| Preparation of Oral Liquid (Syrup) | |
|---|---|
| Ingredient | % W/V |
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 7

| Preparation of Oral Liquid (Elixir) | |
|---|---|
| Ingredient | % W/V |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 8

| Preparation of Oral Suspension (Syrup) | |
|---|---|
| Ingredient | % W/V |
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 9

| Preparation of Injectable Solution | |
|---|---|
| Ingredient | % W/V |
| Active Compound | 0.05–5 |
| Benzyl Alcohol N.F. | 0.9 |
| Water for Injection | 100.0 |

EXAMPLE 10

| Preparation of Injectable Oil | |
|---|---|
| Ingredient | % W/V |
| Active Compound | 0.05–5 |
| Benzyl Alcohol | 1.5 |
| Sesame Oil qs ad | 100.0 |

EXAMPLE 11

| Preparation of Intra-Articular Product | |
|---|---|
| Ingredient | Amount |
| Active Compound | 2–20 mg |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 12

| Preparation of Injectable Depo Suspension | |
|---|---|
| Ingredient | % W/V |
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs |
| Water for Injection qs ad | 100.0 |

The compounds of the present invention may be administered internally, e.g., orally, intra-articularly or parenterally, e.g., intra-articular, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

While in general the sodium salts of the acids of the invention are suitable for parenteral use, other salts may also be prepared, such as those of primary amines, e.g., ethylamine; secondary amines, e.g., diethylamine or diethanol amine; tertiary amines, e.g., pyridine or triethylamine or 2-dimethylaminomethyl-dibenzofuran; aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore as well as the sodium salt, those of the alkali metals, such as potassium and lithium; of ammonia; and of the alkaline earth metals, such as calcium or magnesium, may be employed. It will be apparent, therefore, that these salts embrace, in general derivatives of salt-forming cations.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form, as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test, Code 026 (C1 inhibitor). This test measures the ability of activated human C1 to destroy fluid phase human C2 in the presence of C4 and appropriate dilutions of the test compound. An active inhibitor protects C2 from C1 and C4; (ii) Test, Code 035 (C3-C9 inhibitor) - This test determines the ability of the late components of human complement (C3-C9) to lyse EAC 142 in the presence of appropriate dilutions of the test compound. An active inhibitor protects EAC 142 from lysis by human C3-C9; (iii) Test, Code 036 (C-Shunt inhibitor) — In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test - Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/ is then reported, unless otherwise stated; (v) Forssman Shock Test — Lethal shock is produced in guinea pigs by an i.v. injection of anti-Forssman antiserum and the harmonic mean death time of treated guinea pigs is compared with that of simultaneous controls; (vi) Complement Level Reduction Test — In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test — Here, appropriate amounts of the test compound are added to a pool of guinea pig serum in vitro, after which the undiluted serum capillary tube assay referred to above is run. The concentration of compound inhibiting 50% is reported.

With reference to Table I, guinea pigs weighing about 300 g were dosed intravenously (i.v.) or intraperitoneally (i.p.) with 200 mg/kg of the test compound dissolved in saline and adjusted to pH 7-8. One hour after dosing, the guinea pigs were decapitated, blood was collected and the serum separated. The serum was tested for whole complement using the capillary tube assay. Percent inhibition was calculated by comparison with simultaneous controls. The results appear in Table I together with results of tests, code 026, 035, 036, Cap 50, % inhibition and Forssman shock. Table I shows that the compounds of the invention possess highly significant in situ and in vivo, complement inhibiting activity in warm-blooded animals.

TABLE I

| Biological Activities | | | |
|---|---|---|---|
| | In Vitro Activity | | |
| Compound | C1 026* Wells | C-Late 035* Wells | Shunt Inhibition 036* Wells |
| 2,2',2"-[s-Phenenyltris(sulfonylimino)]-tris[2-deoxy-α-D-glucopyranose], dodecakis (H-sulfate) dodecasalt with trimethylamine | +7** | N | +2 |
| 2,2',2"-[s-Phenenyltris(sulfonylimino)]-tris[2-deoxy-α-D-glucopyranose], dodecakis (H-sulfate) dodecasodium salt | +7 | N | +1 |

N = negative
*Code designation for tests employed as referred to herein.
**Activity in wells a serial dilution assay. Higher well numbers indicates higher activity. The serial dilutions are two-fold.

We claim:

1. A compound of the formula:

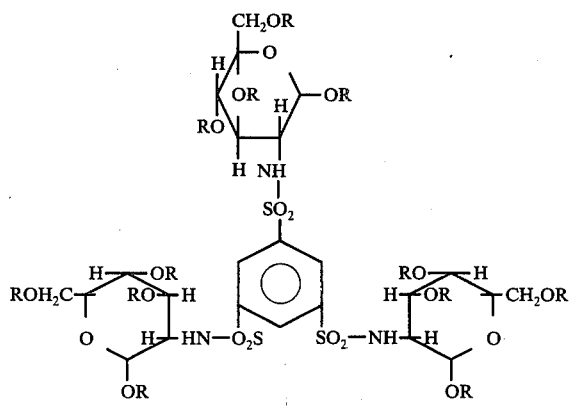

wherein R is a moiety selected from the group consisting of —SO$_3$H.N(CH$_3$)$_3$ and —SO$_3$X, wherein X is selected from the group consisting of alkali metal; and the pharmaceutically acceptable salts thereof.

2. A compound according to claim 1, wherein R is the moiety —SO$_3$X, wherein X is as previously defined.

3. The compound according to claim 1, 2,2',2"-[s-phenenyltris(sulfonylimino)]tris[2-deoxy-α-D-glucopyranose], dodecakis (H-sulfate) dodecasalt with trimethylamine.

4. The compound according to claim 1, 2,2',2''-[s-phenenyltris(sulfonylimino)]tris[2-deoxy-α-D-glucopyranose], dodecakis (H-sulfate) dodecasodium salt.

5. The compound 2,2',2''-[s-phenenyltris(sulfonylimino)]tris[2-deoxy-D-glucopyranose].

6. A method of inhibiting the complement system in a body fluid which comprises subjecting said body fluid to the action of an effective complement inhibiting amount of a pharmaceutically acceptable compound of the formula:

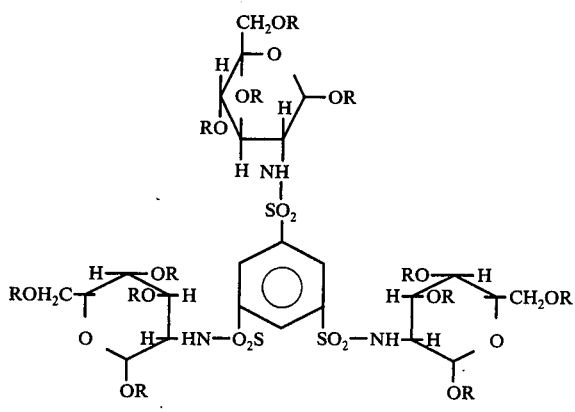

wherein R is a moiety selected from the group consisting of —SO₃H.N(CH₃)₃ and —SO₃X, wherein X is selected from the group consisting of alkali metal; and the pharmaceutically acceptable salts thereof.

7. A method according to claim 6, wherein said compound is 2,2',2''-[s-phenenyltris(sulfonylimino)]tris[2-deoxy-α-D-glucopyranose], dodecakis (H-sulfate) dodecasalt with trimethylamine.

8. A method according to claim 6, wherein said compound is 2,2',2''-[s-phenenyltris(sulfonylimino)]tris[2-deoxy-α-D-glucopyranose], dodecakis (H-sulfate) dodecasodium salt.

9. A method according to claim 6, wherein said body fluid is blood serum.

10. A method of inhibiting the complement system in a warm-blooded animal which comprises internally administering to said animal an effective complement inhibiting amount of a pharmaceutically acceptable compound of the formula:

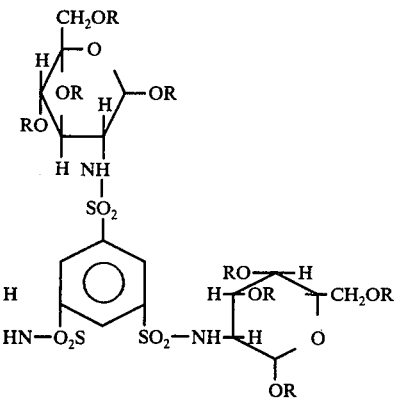

wherein R is a moiety selected from the group consisting of —SO₃H.N(CH₃)₃ and —SO₃X, wherein X is selected from the group consisting of alkali metal; and the pharmaceutically acceptable salts thereof.

11. A method according to claim 10, wherein said compound is 2,2',2''-[s-phenenyltris(sulfonylimino)]tris[2-deoxy-α-D-glucopyranose], dodecakis (H-sulfate) dodecasalt with trimethylamine.

12. A method according to claim 10, wherein said compound is 2,2',2''-[s-phenenyltris(sulfonylimino)]tris[2-deoxy-α-D-glucopyranose], dodecakis (H-sulfate) dodecasodium salt.

13. A method according to claim 10, wherein said compound is administered intra-articularly.

14. A method for the preparation of a compound of the formula:

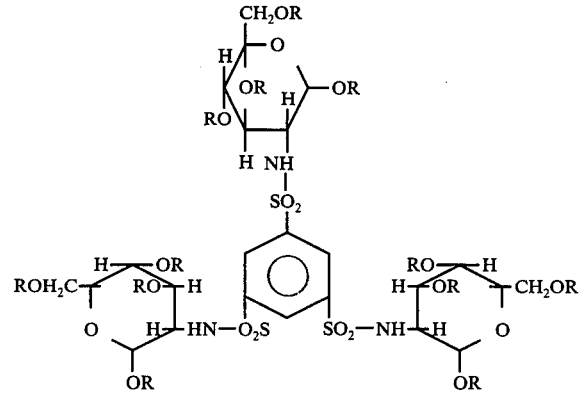

wherein R is a moiety selected from the group consisting of —SO₃H.N(CH₃)₃ and —SO₃X, wherein X is selected from the group consisting of alkali metal; and the pharmaceutically acceptable salts thereof; which comprises reacting tetra-o-acetyl glucosamine with 1,3,5-benzenetrisulfonyl chloride in a weakly basic polar solvent; concentrating said solvent and precipitating the tetraacetyl trisulfonyl derivative from ice water and extracting into methylene dichloride; evaporating said solvent and dissolving said derivative in cold C₁-C₆ alkanol saturated with ammonia; chilling for 24 hours, introducing nitrogen gas to remove ammonia, and evaporating to a thick oil; purifying said oil from water with activated charcoal, filtering and then drying to afford 2,2',2''-[s-phenenyltris(sulfonylimino)]tris[2-deoxy-D-glucopyranose]; reacting said glucopyranose with trimethylamine sulfur trioxide in dimethylformamide at 65° to 70° for 18 hours, and precipitating from C₁-C₆ alkanol to afford 2,2',2''-[s-phenenyltris(sulfonylimino)]tris[2-deoxy-α-D-glucopyranose], dodecakis (H-sulfate) with trimethylamine and treating said trimethylammonium salt with sodium acetate in an aqueous medium for several minutes, and precipitating from C₁-C₆ alkanol to afford 2,2',2''-[s-phenenyltris(sulfonylimino)]tris[2-deoxy-α-D-glucopyranose], dodecakis (H-sulfate) dodecasodium salt.

* * * * *